(12) United States Patent
Powers et al.

(10) Patent No.: US 7,794,941 B2
(45) Date of Patent: Sep. 14, 2010

(54) ROLE OF FGF-20 IN CANCER DIAGNOSIS AND TREATMENT

(75) Inventors: Scott Powers, Cold Spring Harbor, NY (US); Lars Zender, Cold Spring Harbor, NY (US); Rebecca A. Kohnz, Cold Spring Harbor, NY (US); Scott W. Lowe, Cold Spring Harbor, NY (US)

(73) Assignee: Cold Spring Harbor Laboratory, Cold Spring Harbor, NY (US)

( * ) Notice: Subject to any disclaimer, the term of this patent is extended or adjusted under 35 U.S.C. 154(b) by 11 days.

(21) Appl. No.: 11/893,086

(22) Filed: Aug. 13, 2007

(65) Prior Publication Data

US 2008/0188434 A1     Aug. 7, 2008

Related U.S. Application Data

(60) Provisional application No. 60/837,007, filed on Aug. 11, 2006.

(51) Int. Cl.
*C12Q 1/68* (2006.01)
*C12P 19/34* (2006.01)

(52) U.S. Cl. .......................................... 435/6; 435/91.2
(58) Field of Classification Search ........................ None
See application file for complete search history.

(56) References Cited

U.S. PATENT DOCUMENTS 6,797,695 B1     9/2004     Itoh et al.

FOREIGN PATENT DOCUMENTS

WO     WO 2004/029219     4/2004

OTHER PUBLICATIONS

GeneLoc printout, results for Chromosome 8, band p22, printed from http://genecards.weizmann.ac.il/geneloc-bin/display_map.pl on Aug. 24, 2009; thirteen pages.*
Pils et al. Cancer. 2005; 104:2417-29.*
Weber-Mangel et al. (Int. J. Cancer: 107, 583-592 (2003)).*
Dumur et al. Genomics 81(2003) 260-269.*
Mao et al. (Blood (Feb. 15, 2003) vol. 101, No. 4, p. 1513-1519).*
Garcia et al. (Leukemia (2003) 17, 2016-2024).*
Alvarez et al., "Preclinical characterization of CG53135 (FGF-20) in radiation and concomitant chemotherapy/radiation-induced oral mucositis," *Clin Cancer Res*, 9:3454-3461 (2003).
Bryan et al., "Ductal carcinoma in situ with basal-like phenotype: a possible precursor to invasive basal-like breast cancer," *Mod Pathol*, 19:617-621 (2006).
Cantara et al., "Opposite effects of beta amyloid on endothelial cell survival: role of fibroblast growth factor-2 (FGF-2)," *Pharmacol Rep*, 57:Suppl. 138-143 (2005).
Cappellen et al., "Frequent activating mutations of FGFR3 in human bladder and cervix carcinomas," *Nat Genet*, 23:18-20 (1999).
Chamorro et al., "FGF-20 and DKK1 are transcriptional targets of β-catenin and FGF-20 is implicated in cancer and development," *Embo J*, 24:73-84 (2005).
Gibson et al., "A novel method for real time quantitative RT-PCR," *Genome Res.*, 6:995-1001 (1996).
Itoh et al., "Evolution of the Fgf and Fgfr gene families," *Trends Genet*, 20:563-569 (2004).
Jeffers et al., "Identification of a novel human fibroblast growth factor and characterization of its role in oncogenesis," *Cancer Res*, 61:3131-3138 (2001).
Katoh et al., "Comparative genomics on FGF20 orthologs," *Oncol Rep.*, 14:287-290 (2005).
Lucito et al., "Representational oligonucleotide microarray analysis: a high-resolution method to detect genome copy number variation," *Genome Res.*, 13:2291-2305 (2003).
Nielsen et al., "Immunohistochemical and clinical characterization of the basal-like subtype of invasive breast carcinoma," *Clin Cancer Res*, 10:5367-5374 (2004).
Ornitz et al., "Fibroblast growth factors," *Genome Biol*, 2:reviews3005.1-3005.12 (2001).
Richelda et al., "A novel chromosomal translocation t(4; 14)(p16.3; q32) in multiple myeloma involves the fibroblast growth-factor receptor 3 gene," *Blood*, 90:4062-4070 (1997).
Scherer et al., "Approaches for the sequence-specific knockdown of mRNA," *Nature Biotechnology*, 21:1457-1465 (2003).
Sebat et al., "Large-scale copy number polymorphism in the human genome," *Science*, 305:525-528 (2004).
Valta et al., "Regulation of osteoblast differentiation: a novel function for fibroblast growth factor 8," *Endocrinology*, 147: 2171-2182 (2006).
van de Vijver et al., "A gene-expression signature as a predictor of survival in breast cancer," *N. Engl J Med*, 347:1999-2009 (2002).
Wu et al., "Diverse mechanisms of β-Catenin deregulation of ovarian endometrioid adenocarcinomas," *Cancer Res*, 61:8247-8255 (2001).
Xiao et al., "FGFR1 is fused with a novel zinc-finger gene, ZNF198, in the t(8;13) leukaemia/lymphoma syndrome," *Nat Genet* 18:84-87 (1998).
Genbank Submission; NIH/NCBI, Accession No. NM_019851; Mizuta et al.; Jul. 13, 2008. 3 pages.
Genbank Submission; NIH/NCBI, Accession No. NM_181723; Gerhard et al.; Feb. 11, 2008. 4 pages.

\* cited by examiner

*Primary Examiner*—Juliet C Switzer
(74) *Attorney, Agent, or Firm*—Wolf, Greenfield & Sacks, P.C.

(57) ABSTRACT

The invention provides methods for diagnosing cancers in humans by detecting DNA amplifications in chromosomal region 8p22, which encompasses the FGF-20 gene and the EFHA2 gene. Also provided are cancer treatment methods using inhibitors of FGF-20 and EFHA2. The invention also provides methods for promoting successful regeneration of liver function. These methods can be used therapeutically to improve liver function following transplantation in both recipient and donor subjects.

12 Claims, 7 Drawing Sheets

FIGURE 4
 
Negative Tumor — Positive Tumor

ROLE OF FGF-20 IN CANCER DIAGNOSIS AND TREATMENT

RELATED APPLICATIONS

This Application claims the benefit under 35 U.S.C. §119 (e) of the filing date of U.S. Provisional Application Ser. No. 60/837,007, entitled "ROLE OF FGF-20 IN CANCER DIAGNOSIS AND TREATMENT" filed on Aug. 11, 2006, which is herein incorporated by reference in its entirety.

BACKGROUND OF THE INVENTION

Fibroblast growth factor 20 (FGF-20) is a member of the fibroblast growth factor (FGF) family of secreted growth factors, a large group of growth factors found in organisms as diverse as *C. elegans* and *H. sapiens* (Itoh et al., 2004, Trends Genet 20:563-9). The FGF proteins identified to date belong to a family of signaling molecules that regulate growth and differentiation of a variety of cell types.

In vertebrates, there are twenty-two members of this family that differentially activate four distinct FGF receptors, playing distinct roles in the regulation of proliferation, migration, and differentiation during embryonic development (Ornitz et al., 2001, Genome Biol 2:REVIEWS3005). In adult tissues, FGF molecules function in injury and tissue repair, and many of them are overexpressed in cancer cell lines and can malignantly transform 3T3 cells when overexpressed (Ornitz et al., supra). In humans, three of the four genes for FGF receptors undergo mutational activation in different forms of cancer (Cappellen et al., 1999, Nat Genet 23:18-20; Richelda et al., 1997, Blood 90:4062-70; Xiao et al., 1998, Nat Genet 18:84-7).

Human FGF-20 was identified by three groups. One group discovered it based on its homology to *Xenopus* XFGF-20, which was first identified based on homology to *Xenopus* XFGF-9 (Kirikoshi et al., 2000, Biochem Biophys Res Commun 274:337-43; Koga et al., 1999, Biochem Biophys Res Commun 261:756-65). Another group identified FGF-20 using degenerate PCR primers in a search for novel FGFs and discovered the preferential expression of FGF-20 in the substantia nigra pars compacta of the brain (Ohmachi et al., 2000, Biochem Biophys Res Commun 277:355-60). This group also found that recombinant FGF-20 enhanced the survival of dopaminergic neurons, showing for the first time that a neurotrophic factor was preferentially expressed in brain tissue damaged by Parkinson's disease. See, U.S. Pat. No. 6,797,695. The third group identified FGF-20 by mining the human genome sequences. They showed that ectopic expression of FGF-20 promoted proliferation and transformed NIH-3T3 cells, and that three out of approximately sixty human cancer cell lines expressed abnormally high levels of FGF-20 (Jeffers et al., 2001, Cancer Res 61:3131-8). These attributes are not unique to FGF-20, since almost all FGFs tested show these properties.

Ectopic administration of recombinant FGF-20 has been shown to attenuate the development of inflammatory bowel disease in a rodent model, in part by promoting the proliferation and/or survival of intestinal epithelial cells (Jeffers et al., supra). Moreover, administration of recombinant FGF-20 prevents the formation of oral mucositis in hamsters receiving chemotherapy (Alvarez et al., 2003, Clin Cancer Res 9:3454-61).

FGF-20 has also been shown in gene expression microarray experiments to be a potential downstream target of β-catenin, a human oncogene that lies downstream in the Wnt signaling pathway (Chamorro et al., 2005, Embo J 24:73-84). FGF-20 has also been shown to be a potential target for β-catenin in rat epithelial cells transformed by mutant β-catenin as well as in primary human ovarian endometrioid adenocarcinomas with Wnt pathway defects (Wu et al., 2001, Cancer Res 61:8247-55). Knockdown of FGF-20 by RNA interference (RNAi) in rat epithelial cells blocks the ability of β-catenin to induce anchorage-independent growth, an in vitro correlate of tumorigenicity (Chamorro et al., supra). However, in these studies, FGF-20 was not always upregulated in tumors with Wnt/β-catenin activation.

Comparative genomics analyses on FGF-20 orthologs have shown that FGF-20 is well conserved among vertebrates. For example, the zebrafish FGF-20 gene shows 76.9%, 76.4%, 76.0% and 75.5% amino-acid identity with human, *Xenopus*, rat and mouse FGF-20, respectively (Katoh et al., 2005, Oncol Rep. 14:287-90). Human FGF-20 links to the EF hand domain family, member A2 (EFHA2) gene in a head-to-head manner with an interval of about 25 kb. EFHA2 is a gene of unknown biological function. The FGF20-EFHA2 locus at human chromosome 8p22 and the FGF9-EFHA1 locus at human chromosome 13q12.11 are paralogous regions (paralogons) within the human genome (Katoh et al., supra)

SUMMARY OF THE INVENTION

The present invention is based on the discovery that human chromosome 8p22 is amplified in a number of cancers, including breast, liver and lung cancers, and that FGF-20 and EFHA2 are driver oncogenes of that amplicon. That is, FGF-20 and EFHA2 are genes in that amplicon responsible, separately or together, for the transformation of affected cells. We have also discovered that inhibition of FGF-20 activity inhibits the growth of cancer cells.

Accordingly, the invention provides diagnostic methods for identifying cancer or susceptibility to cancer in a human patient by detecting amplifications of the 8p22 region. One of such methods comprises providing a DNA sample from a tissue (e.g., liver, lung, breast, colon, or blood) of the patient, and detecting, in the DNA sample, amplification of a nucleic acid sequence in chromosomal region 8p22, wherein amplification in this region indicates that the patient has, or is susceptible of developing, cancer in this tissue. Thus, one can diagnose liver, lung, breast, colon and blood cancers (e.g., acute myeloid leukemia and lymphomas). Markers for detecting the amplification can be an FGF-20 gene (i.e., a nucleotide sequence from the FGF-20 gene) and/or an EFHA2 gene (i.e., a nucleotide sequence from the EFHA2 gene). The markers may be 20 nucleotides in length or longer.

This invention also provides methods for selecting a cancer patient for FGF-20 or EFHA2 based treatment. These methods will allow selection of patients who are more likely to respond to cancer treatments with FGF-20 or EFHA2 inhibitors (e.g., antibodies, antisense RNAs or RNAi molecules). One of such methods comprises detecting ampflication of the 8p22 region in the cancer tissue of the patient, wherein amplification in this region indicates that the patient will likely be responsive to the treatment.

We have also discovered that amplification of the 8p22 region often occurs in the basal subtype of breast cancer. Accordingly, the invention provides a method of treating this subtype of breast cancer by inhibiting the expression or activity of FGF-20 using, e.g., an anti-FGF-20 antibody (including a whole, monoclonal antibody, or an antigen-binding fragment thereof, e.g., the Fab fragment, F(ab)'$_2$, Fv, single chain antibody), RNAi molecules, and antisense molecules.

The invention also provides non-human animals that are useful for understanding cancer and its treatments. These animals are transgenic or chimeric animals some of whose cells (e.g., lung, liver, breast or colon cells) over-express FGF-20 and/or EFHA2. These animals are susceptible to developing cancer in tissues containing those cells. Those cells can further contain a genetic mutation (e.g., another activated oncogene (ras, Akt, or myc) or a defect in a tumor suppressor gene, like p53 and PTEN) that makes them even more susceptible to cancer.

We have further discovered that enhanced FGF-20 activation promotes liver regeneration in a patient following a liver transplant, in both recipient and donor patients. Accordingly, this invention also provides methods for promoting successful regeneration of liver function. The methods of the invention can be used to study the effects of altered FGF-20 on the development of liver cell renewal and the promotion of liver cell proliferation and/or survival in the post replication phase. These methods can be used therapeutically to improve liver function following transplantation in both recipient and donor subjects.

BRIEF DESCRIPTION OF THE DRAWINGS

FIG. 4 is a panel of two photographs showing the images of stained human breast cells. Immunohistochemical detection of FGF-20 overexpression in human breast cancer. FGF-20 protein is overexpressed in human breast cancer cells as assayed by immunocytochemistry using commercially available antibodies. On the left is a negative tumor, on the right a positive tumor is shown, surrounded by stromal tissue that is negative.

DETAILED DESCRIPTION OF THE INVENTION

Figure 1:
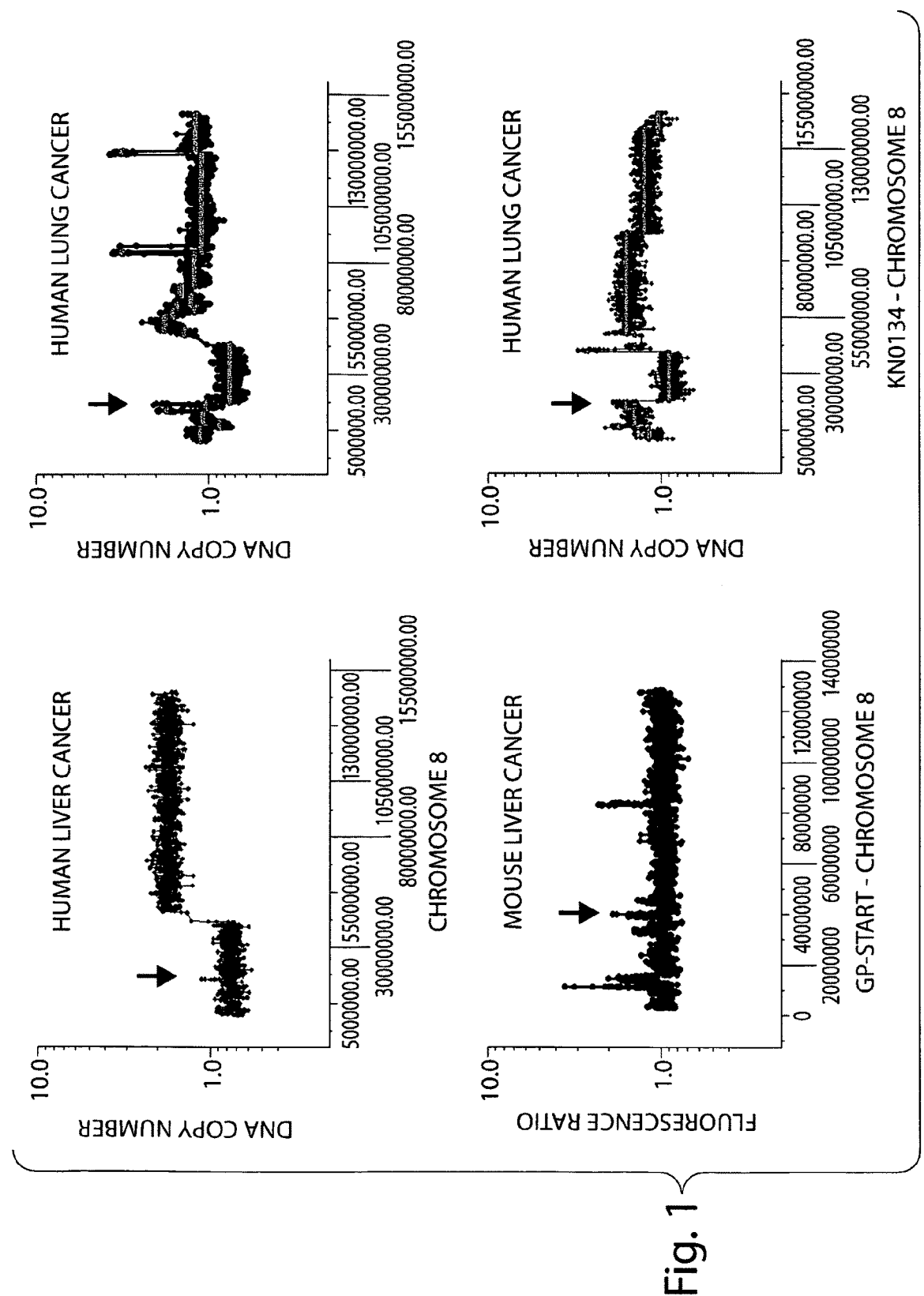
FIG. 1 is a panel of diagrams showing DNA amplicons containing FGF-20. Shown on the left are the representative profiles of human and mouse liver cancers that contain an amplification on chromosome 8. Shown in the right are representative profiles of human lung tumors that contain an amplification on chromosome 8.

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures used in connection with, and techniques of, cell and tissue culture, molecular biology, cell and cancer biology, virology, immunology, microbiology, genetics and protein and nucleic acid chemistry described herein are those well known and commonly used in the art.

The methods and techniques of the present invention are generally performed according to conventional methods well known in the art and as described in various general and more specific references that are cited and discussed throughout the present specification, unless otherwise indicated. See, e.g., Sambrook et al., Molecular Cloning: A Laboratory Manual, 2d ed., Cold Spring Harbor Laboratory Press, Cold Spring Harbor, N.Y. (1989); Ausubel et al., Current Protocols in Molecular Biology, Greene Publishing Associates (1992, and Supplements to 2003); Harlow and Lane, Antibodies: A Laboratory Manual, Cold Spring Harbor Laboratory Press, Cold Spring Harbor, N.Y. (1990); Coffin et al., Retroviruses, Cold Spring Harbor Laboratory Press; Cold Spring Harbor, N.Y. (1997); Bast et al., Cancer Medicine, 5th ed., Frei, Emil, editors, BC Decker Inc., Hamilton, Canada (2000); Lodish et al., Molecular Cell Biology, 4th ed., W. H. Freeman & Co., New York (2000); Griffiths et al., Introduction to Genetic Analysis, 7th ed., W. H. Freeman & Co., New York (1999); Gilbert et al., Developmental Biology, 6th ed., Sinauer Associates, Inc., Sunderland, Mass. (2000); and Cooper, The Cell—A Molecular Approach, 2nd ed., Sinauer Associates, Inc., Sunderland, Mass. (2000). All of the above and any other publications, patents and published patent applications referred to in this application are specifically incorporated by reference herein.

The invention provides diagnostic methods of detecting human cancer or susceptibility to cancer based on copy number amplification of a nucleotide sequence from the chromosomal 8p22 region. The amplified genomic region is also called an amplicon. Since we have found that the FGF-20 gene, and potentially the EFHA2 gene, are the driver oncogenes of the 8p22 amplicon, preferred markers for the diagnostic methods of the present invention are nucleotide sequences from the FGF-20 gene (e.g., GenBank Accession No. NM_019851) and the EFHA2 gene (e.g., GenBank Accession No. NM_181723).

Detection of 8p22 amplification is also useful in stratifying cancer patients for their responsiveness to FGF-20-based or EFHA2-based treatment. It is well known in cancer biology that not all patients of a particular type of cancer respond in the same way to a given therapy, and that responsiveness to a therapy is related at least in part to the genetic makeup of the cancer. A pre-treatment assessment of a patient of cancer genetic characteristics will therefore improve the success rate of the treatment. Given that the 8p22 amplicon exists in only a subset of cancer patients, it is useful to confirm its existence in patients who are to receive a cancer therapy based on an FGF-20 or EFHA-2 inhibitor.

Genomic profiling as done by microarray analysis can be used to detect DNA amplifications. One such method is Representational Oligonucleotide Microarray Analysis (ROMA), a genome-wide scanning method capable of identifying copy number alterations in cells at high resolution (Lucito et al., 2003, Genome Res. 13:2291-2305; Sebat et al., 2004, Science 305:525-528). One can also use, e.g., the GENECHIP arrays, the SNP arrays, and the EXON arrays available from Affymetrix to perform microarray analysis of genomic profiles for detecting 8p22 amplification. Other methods for detecting amplification in the 8p22 region includes quantitative polymerase chain reaction (PCR), Southern blotting, and dot blotting, using primers and/or probes from the 8p22 region, e.g., those derived from the FGF-20 and EFHA2 genes. The primers and probes may hybridize to a genomic sequence that encodes the entirety or part (e.g., at 20, 25, 35, or 40 contiguous nucleotides) of the FGF-20 or EFHA2 gene, including allelic variants of the gene. Preferably, the primers and probes hybridize to a relatively unique part of the gene so as to reduce background noise signal. Genomic DNA from a normal individual or from a healthy tissue of the cancer patient can be used as a control for detecting amplification.

The present invention provides methods of targeted therapies for a variety of cancers, including lung, breast, liver, and colon cancers. Targeted therapies are based on the premise that cancer cells require continuous oncogenic signaling for survival and proliferation. Thus, drugs that terminate or disrupt this signaling remove the stimuli for cancer growth. A targeted therapy directly interferes with a driver oncogene and can be effected by, e.g., monoclonal antibodies (humanized or chimeric), cancer vaccines, and gene therapy (including RNA interference, antisense and ribozyme technology).

None of the twenty-two FGF genes were previously known to be activated by mutation or amplification in human cancers. The present discovery that FGF-20 is the driver oncogene in the 8p22 amplicon provides a rationale for targeting FGF-20 in cancer therapy, at least for 8p22 amplicon-positive patients and for patients harboring mutations of genes that are in the FGF-20 signaling pathway, such as those in the Wnt/β-catenin pathway. Inhibitors of FGF-20 are discussed below. In some embodiments, a combination of FGF-20 and EFHA2 inhibitors are used.

The FGF-20 and/or EFHA-2 targeted therapy can also be used in conjunction with a traditional cancer therapy that targets growth factors and their receptors such as epidermal growth factor receptor (EGFR) (e.g., a Gefitinib, Erlotinib, or Imatinib therapy) or vascular epidermal growth factor (VEGF) (e.g., bevacizumab (AVASTIN®)). The targeted therapy of this invention can also be used in conjunction with chemotherapies such as Taxanes (a group of drugs that includes paclitaxel (TAXOL®) and docetaxel (TAXOTERE®)), Cisplatinin, Methotrexate, and 5-fluorouracil. The targeted therapy and combination therapy of this invention will inhibit growth of cancer cells and can reduce tumor size, cause tumor regression, prevention of metastasis, and prevention of angiogenesis at tumor sites.

The targeted therapy of this invention is particularly useful in treating lung, colon, breast and liver cancers, where 8p22 amplification has been observed to occur at a relatively high rate. Cancers treatable by the therapy include malignant tumors, pre-malignant conditions such as proliferative and cellular hyperplasia, neoplasm, and metastasized cancer.

Two distinct types of epithelial cells are found in the human mammary gland: basal (and/or myoepithelial) cells and luminal epithelial cells (Taylor-Papadimitriou et al., 1989, J. Cell Sci. 94:403-413). These two cell types can be distinguished immunohistochemically—basal epithelial cells can be stained with antibodies to keratin 5/6, whereas luminal epithelial cells can be stained with antibodies to keratin 8/18 (Perou et al., 2000, Nature 406(6797):747-52). The basal cells can also be identified by gene expression profiling and cluster analysis. Id. The luminal A and basal-like subtypes of breast cancer are the two main subtypes of breast cancer, each of which represents a biologically distinct disease. We have discovered that 8p22 amplification occurs at a particular high rate in the basal subtype of breast cancer, as compared to other subtypes of breast cancers.

Inhibitors of FGF-20 are known in the art or can be developed by well established methods. For example, FGF-20 activity can be inhibited by disrupting the nucleic acid sequence that encodes the gene, e.g., by antisense technology, RNA interference techniques, and ribozyme technology. FGF-20 activity can be determined by examining the cells for the expression of specific gene products by PCR, Northern blots and the like; or for the production of the polypeptides encoded by the targeted gene by using Western blots and other immunoassays. FGF-20 activity can also be inhibited by using, e.g., small molecules that bind FGF-20, anti-FGF-20 antibodies, or peptide mimetics of FGF-20 or receptor thereof.

Antibodies to FGF-20 like those that have been raised against different FGFs are useful for the targeted therapy of this invention (e.g., Valta et al., 2006, Endocrinology 147: 2171-82; Cantara et al., 2005, Pharmacol Rep 57:138-43). The FGF-20 specific antibodies are preferably administered together with a pharmaceutically acceptable carrier.

Both polyclonal and monoclonal antibodies that bind FGF-20 or EFHA2 can be used. The antibodies can be specific for linear epitopes, discontinuous epitopes, or conformational epitopes of 5 or more amino acid residues on FGF-20 or EFHA2. In general, an antibody of this invention refers to a full antibody, e.g., an antibody comprising two heavy chains and two light chains, or to an antigen-binding fragment of a full antibody. Such fragments include, but are not limited to, those produced by digestion with various proteases, those produced by chemical cleavage and/or chemical dissociation, and those produced recombinantly, so long as the fragment remains capable of specific binding to the antigen. Among these fragments are Fab, Fab', F(ab')$_2$ and single chain Fv (scFv) fragments.

Fragments of at least five, usually at least eight contiguous amino acids, often at least fifteen contiguous amino acids, can be used as immunogens for raising FGF-20 and EFHA2 antibodies.

The FGF-20 and EFHA2 inhibitors can be antisense molecules that specifically hybridize to FGF-20 and EFHA2 sense polynucleotides. The antisense nucleic acid molecule can be complementary to the entire coding or non-coding region of FGF-20, but more often is an oligonucleotide that is antisense to only a portion of the coding or non-coding region of FGF-20 mRNA. For example, the antisense oligonucleotide can be complementary to the region surrounding the translation start site of FGF-20 mRNA. An antisense oligonucleotide can be, for example, about 5, 10, 15, 20, 25, 30, 35, 40, 45 or 50 nucleotides in length.

An antisense target sequence is a nucleotide sequence unique to FGF-20 or EFHA2, and can be identified through use of any publicly available sequence database and antisense design software. Antisense nucleic acids of the invention can then be constructed using procedures known in the art. For example, an antisense nucleic acid (e.g., an antisense oligonucleotide) can be produced biologically using an expression vector into which a nucleic acid has been inserted in an antisense orientation, i.e., RNA transcribed from the inserted nucleic acid will be of an antisense orientation to a target nucleic acid of interest.

The antisense nucleic acid molecules can be administered to a subject (e.g., a human) or generated in situ via an expression vector, such that they bind to cellular RNA and/or genomic DNA encoding an FGF-20 protein to inhibit expression of the protein, e.g., by inhibiting transcription and/or translation. Suppression of FGF-20 expression at either the transcriptional or translational level is useful to treat certain cancer conditions in patients or to generate cellular or animal models for cancer characterized by aberrant FGF-20 expression.

By way of example, an antisense molecule can be administered by direct injection at a tissue site of a subject. Alternatively, an antisense molecule can be designed to target selected cells (e.g., cancer cells overexpressing FGF-20) and then administered systemically; for example, the antisense molecule contains a peptide or antibody that specifically binds to a cell surface receptor or antigen expressed on the surface of the selected cell surface. The antisense nucleic acids can also be delivered to target cells using expression vectors encoding thereof.

The targeted therapy of this invention can also use a RNA interfering molecule that targets FGF-20 or EFHA2 (see, e.g., Chamorro et al., supra, for RNAi against FGF-20; Example 2 below). A RNA interfering molecule often is a short hairpin RNA that is complementary with a portion of a transcript encoded by a target gene. When a nucleic acid construct encoding a short hairpin RNA is introduced into a cell, the cell incurs partial or complete loss of expression of the target gene. In this way, a short hairpin RNA functions as a sequence specific expression inhibitor or modulator in transfected cells. The use of short hairpin RNAs facilitates the down-regulation of FGF-20 and/or EFHA2. The short hairpin RNAs that are useful in the invention can be produced using a wide variety of RNA interference ("RNAi") techniques that are well known in the art. The invention may be practiced using short hairpin RNAs that are synthetically produced as well as microRNA (miRNA) molecules that are found in nature and can be remodeled to function as synthetic silencing short hairpin RNAs. A preferred embodiment of the invention is the use of a short hairpin RNA that mediates inhibition of a oncogenic signal and thus apoptotic signaling in a cell.

Other methods of RNA interference may also be used in the practice of this invention. See, e.g., Scherer and Rossi, 2003, Nature Biotechnology 21:1457-65 for a review on sequence-specific mRNA knockdown of using antisense oligonucleotides, ribozymes, DNAzymes, RNAi and siRNAs. See also, International Patent Application PCT/US2003/030901 (Publication No. WO 2004/029219 A2), filed Sep. 29, 2003 and entitled "Cell-based RNA Interference and Related Methods and Compositions."

The mouse cancer model of this invention is made by altering mouse cells to increase FGF-20 and/or EFHA2 expression and transplanting the resulting cells into a recipient mouse. The spontaneous mutations arising in tumors initiated by different oncogenic lesions are compared to alterations observed in human cancers. For example, altered hepatocytes are transplanted subcutaneously into a non-human animal so as to develop a liver cancer tumor from at least one of the altered hepatocytes, wherein RNAi mediated knockdown of EFHA2 expression suppresses the liver cancer tumors in the model.

Cells can be genetically modified in the methods of the invention by infection with lentiviral or retroviral vectors carrying various genetic alterations, including oncogenes or short hairpin RNAs against tumor suppressor genes. Virally transduced cells can efficiently engraft the liver of non-human animals after transplantation into their portal vein or spleen. In the case of certain genetic configurations, mice developed hepatocellular carcinomas that could be visualized by whole body fluorescence imaging. Overall, it provides rapid generation of genetically defined hepatocellular cancers.

In some embodiments, the invention features a transgenic mouse, whose genome comprises: an expression construct comprising an EFHA2 coding sequence operably linked to an inducible promoter, and a genetic mutation that causes the transgenic mammal to have greater susceptibility to cancer than a mouse not comprising the genetic mutation, where expression of the EFHA2 gene leads to formation of cancer in the transgenic mammal and the cancer regresses when expression of the EFHA2 gene is reduced. Mutations that render the animal more susceptible to cancer include disabling mutations in a tumor suppressor gene and activating mutations in an oncogene. In a related embodiment, the induction of the EFHA2 expression occurs in a tissue-specific manner, i.e., the EFHA2 transgene can be turned on or off only in a particular tissue of the animal; this embodiment allows one to study the development (including maintenance), regression and recurrence of tumor in a selected tissue or organ of the animal as well as the efficacy and tissue toxicity of candidate drugs that target EFHA2.

The invention further provides chimeric mouse comprising the expression construct containing EFHA2 nucleotide sequence; and a genetic mutation that causes said chimeric animal to have greater susceptibility to cancer than an animal not comprising said genetic mutation, wherein expression of the EFHA2-coding nucleic acid leads to formation of cancer in said chimeric animal, and wherein said cancer regresses in said chimeric animal when expression of said EFHA2-coding nucleic acid is reduced. In another embodiment, this invention provides the chimeric animal wherein both somatic and germ cells comprise the EFHA2-coding nucleic acid.

This invention provides a chimeric mouse comprising a disruption of the endogenous EFHA2 gene. In one embodiment, both copies of the endogenous EFHA2 gene are disrupted. In another embodiment, the EFHA2 gene is disrupted in a specific tissue. In yet another embodiment, the EFHA2 gene is disrupted using RNAi. In a further embodiment, the RNAi is constitutive or inducible.

Tumors showing specific amplifications of candidate oncogenes in gene expression profiles can be outgrown in culture. Using stable RNAi, efficient knockdown of these genes can be achieved. Tumor cells with stable knockdown of a previously amplified gene can be re-transplanted into the mouse model of the current invention. Using this approach new therapeutic targets for cancer can be obtained and the specific consequences of knocking down an amplified gene with regard to tumor growth or metastases can be studied. Drug therapies that specifically inhibit the identified targets can be developed.

The term overexpressed, overexpression, enhancement or increase in expression refers to an abundance of an expressed gene product that is higher than the abundance of that same product under other conditions or in other cells or tissues. Overexpression or increased expression may be effected, for example, by one or more structural changes to the gene's encoding nucleic acid or encoded polypeptide sequence (e.g., primary nucleotide or amino acid changes or post-transcriptional modifications such as phosphorylation), altered gene regulation (e.g., in the promoters, regulators, repressors or chromatin structure of the gene), a chemical modification, an altered association with itself or another cellular component, an altered subcellular localization, a modification which causes higher levels of activity through association with other molecules in the cell (e.g., attachment of a targeting domain) and the like.

The term inhibition, underexpressed, underexpression, inhibition or decrease in expression refers to an abundance of an expressed gene product that is lower than the abundance of the same product under other conditions or in other cells or tissues. Such underexpression or decreased expression may be effected, for example, by one or more structural changes to the gene's encoding nucleic acid or polypeptide sequence (e.g., primary nucleotide or amino acid changes or post-transcriptional modifications such as phosphorylation), altered gene regulation (e.g., in the promoters, regulators, repressors or chromatin structure of the gene), an altered structure (which causes reduced levels of activity), an altered association with itself or another cellular component, an altered subcellular localization, a modification which causes reduced levels of activity through association with other molecules in the cell (e.g., binding proteins which inhibit activity or sequestration) and the like.

The size and growth of cancer after therapy can be monitored by a wide variety of ways known in the art. Whole body fluorescence imaging can be used in the animal models of the invention, where the preferred viral vectors of this invention carry a GFP expression cassette. See, e.g, Schmitt et al., 2002, Cancer Cell 1:289-98. Tumors can also be examined histologically. Paraffin embedded tumor sections can be used to perform immunohistochemistry for cytokeratins and ki-67 as well as TUNEL-staining. The apoptotic rate of cells can be analyzed by TUNEL assay according to published protocols (Di Cristofano et al., 2001, Nature Genetics, 27:222-224). A significant regression or inhibition of the cancer in the mouse will indicate that the candidate molecule is useful for treating cancer.

Liver regeneration refers to the process that preferably occurs in response to injury or whole or partial removal of the liver, but can also occur independent of these mechanisms. The liver is the main detoxifying organ of the body and injury by ingested toxins will stimulate liver regeneration. Liver regeneration involves replication of mature liver cells and is not normally mediated by stem cells. Liver regeneration ceases once the liver has attained the mass that is required for the functional needs of the subject.

Hepatocytes include all descendants of embryonic liver progenitor cells and represent the main functional cells within the liver. Hepatocytes can exist in or around the liver. Preferably, primary hepatocytes are used in the animal models of this invention. In the animal models of the invention, hepatocytes can be virally transduced with vectors carrying oncogenes and/or expression cassettes for short hairpin RNAs directed against tumor suppressor genes. Such transductions may be effected using standard and conventional protocols. In the liver regeneration methods of the invention, hepatocytes in and surrounding the liver can proliferate and replicate to reestablish normal liver tissue architecture. This can occur at the stage of hepatocyte proliferation. See, R. Taub, 2004. Liver regeneration: from myth to mechanism. Nat Rev Mol Cell Biol 5:836-47.

An altered hepatocyte refers to a change in the level of a gene and/or gene product with respect to any one of its measurable activities in a hepatocyte (e.g., the function which it performs and the way in which it does so, including chemical or structural differences and/or differences in binding or association with other factors). An altered hepatocyte may be effected by one or more structural changes to the nucleic acid or polypeptide sequence, a chemical modification, an altered association with itself or another cellular component or an altered subcellular localization.

Mature liver cells refer to descendants of liver stem cells, i.e., progenitor cells. In the methods of the invention, mature liver cells replicate during liver regeneration in response to injury or whole or partial removal of the liver. Mature liver cells can exist in or around the liver organ itself.

Therapies that may be tested and evaluated in the methods and models of this invention include both general and targeted therapies. As used herein, a general therapy can be, for example, a pharmaceutical or chemical with physiological effects, such as pharmaceuticals that have been used in chemotherapy for cancer. Chemotherapeutic agents inhibit proliferation of tumor cells, and generally interfere with DNA replication or cellular metabolism. See, e.g., The McGraw-Hill Dictionary of Chemical Terms (Parker, S., Ed., McGraw-Hill, San Francisco (1985)). Chemotherapeutic agents may or may not have been characterized for their target of action in cells. However, this invention and its methods and models allow evaluation of such therapies for defined genetic alterations.

Throughout this specification, the word "comprise" or variations such as "comprises" or "comprising" will be understood to imply the inclusion of a stated integer or group of integers but not the exclusion of any other integer or group of integers.

The following examples are meant to illustrate the methods and materials of the present invention. Suitable modifications and adaptations of the described conditions and parameters normally encountered in the art are within the spirit and scope of the present invention.

EXAMPLE 1

ROMA Identifies Spontaneous Mutations in a Subset of Human and Murine Carcinomas To molecularly characterize human and murine carcinomas, spontaneously acquired lesions in human hepatocellular and lung carcinomas and mouse models of hepatocellular carcinoma were analyzed using ROMA, a genome-wide scanning method capable of identifying copy number alterations in tumor cells at high resolution (Lucito et al., supra). General procedures were followed as outlined in Sebat et al., supra. Each human or mouse ROMA array consisted of 85,000 oligonucleotide probes designed to the UCSC April 2003 draft assembly of the human genome and the UCSC February 2003 draft assembly of the mouse genome, allowing genome scanning at a theoretical resolution of approximately 35 kb.

Genomic representations were produced from DNA obtained from several human hepatocellular and lung carcinomas and mouse hepatocellular carcinoma and from normal human and mouse liver and human lung tissue. The representations were fluorescently labeled and hybridized to the ROMA microarrays. The data derived after scanning were normalized as described (Sebat et al., supra). The FGF-20 gene was identified as a candidate amplified human oncogene during the cross-comparison of genomic alterations of both human hepatocellular and lung carcinomas and mouse models of hepatocellular and lung carcinoma. Being found in both human and mouse tumors is a strong indication that its amplification in human tumors is meaningful and not due to the background level of DNA amplification caused by genomic instability.

Figure 2:
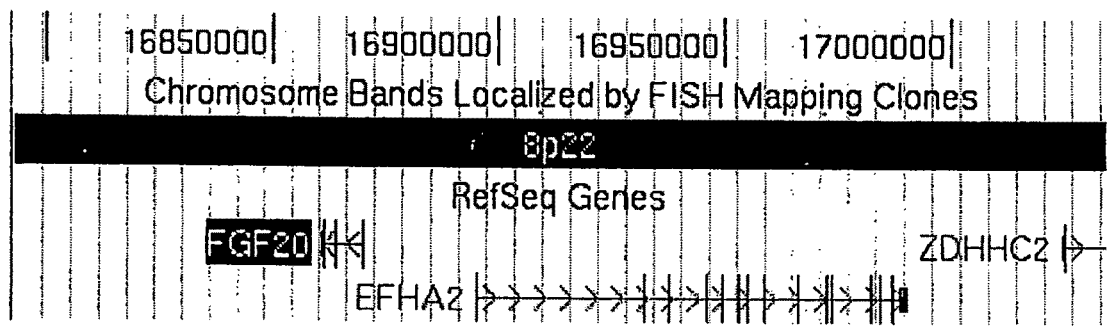
FIG. 2 is a schematic diagram showing chromosome bands localized by FISH mapping clones. Gene content of the 241 kb human liver amplicon on chromosomal region 8p22; minimal overlap region contains genes indicated. The amplicon spanned chromosome 8 nucleotide position 16,826,859-17,068,040 (NCBI Build 34), and overlapped the two human lung amplicons, which are larger, as well as overlapping the syntenic region that is amplified in the mouse tumor. The two intact genes within this region are FGF-20 and EFHA2.

Amplicons often contain more than one gene, and experimental work is necessary to determine which of the genes has oncogenic function. Before embarking on this time-intensive effort, we first determined the common region of amplification shared by all tumors that displayed amplification in region containing FGF-20. In this case, the common region was defined by the smallest amplicon—the one found in the human liver tumor in the upper left panel of FIG. 1 and the gene content shown in FIG. 2.

ROMA analysis of liver and lung cancers identified a focal amplicon on chromosome 8p22 in each of the tumors. The 241 kb amplicon spanned chromosome 8 nucleotide position 16,826,859-17,068,040 (NCBI Build 34), and overlaps the two human lung amplicons, which are larger, as well as overlapping the syntenic region that is amplified in the mouse tumor. The two intact genes within this region are FGF-20 and EFHA2. An incomplete 5' region of ZDHHC2, containing only 5' non-coding sequence, is also within this region, but could not possibly express a functional protein. Additionally, there are no known or predicted RNA genes, including microRNAs, in this region. These results demonstrate that it is FGF-20 or EFHA2 that is the driver oncogene of the 8p22 chromosomal amplification in human and murine cancer. EFHA2 is a gene of previously unknown biological function. These cross-species comparison suggests that a gene(s) within this recurrent 8p22 amplified region is crucial for tumorigenesis in certain contexts.

EXAMPLE 2

Effects of FGF-20 Suppression on Liver Tumor Growth In Vivo

To determine if the driver gene of the amplicon described in Example 1 was FGF-20, we took advantage of the fact that the mouse liver tumor that contained the FGF-20 amplicon is transplantable, so we were able to test what would happen to its ability to form tumors again if FGF-20 was knocked down with RNAi. In order to examine whether FGF-20 was required to sustain tumor growth, the impact of reducing FGF-20 levels on the growth of liver tumors was tested in vivo.

Hepatoblast cultures were injected subcutaneously into the back of nude mice to facilitate precise measurement of liver tumor growth. Two different shRNA constructs from the Hannon/Elledge library were used to suppress FGF-20 expression by RNA interference. The best performing shRNAs were co-introduced into outgrown liver tumor cells.

Figure 3:
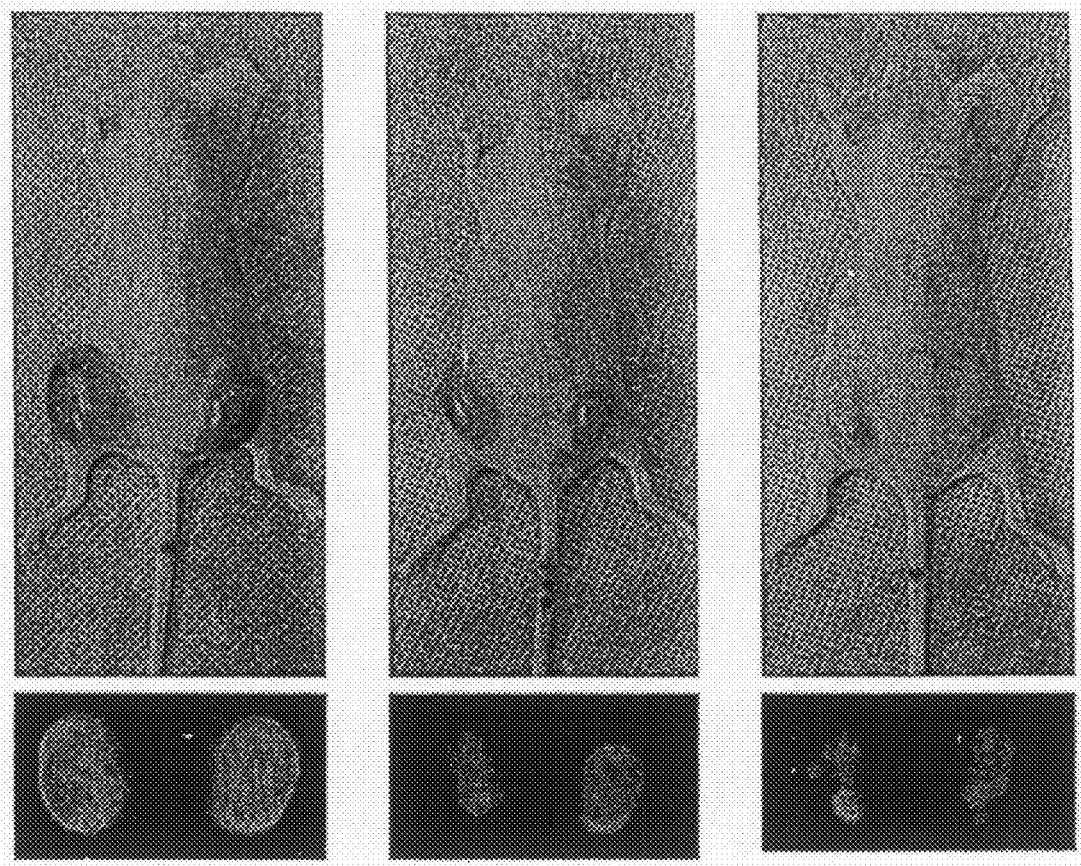
FIG. 3 is a panel of photographs showing mice with liver tumors. RNAi mediated knockdown of FGF20 expression suppresses the tumorigenicity of a mouse liver tumor transplanted subcutaneously back into the animal. Representative example of a tumor infected with a retrovirus expressing a short hairpin RNA directed against FGF-20 (middle and right) compared to a control vector infected tumor (left). Tumor size was assessed by caliper measurement of subcutaneously growing tumors. External GFP-imaging of the tumors (bottom) was performed at the same time post-injection.

As shown in FIG. 3, there was a strong effect of knocking down FGF-20 expression on tumorigenicity. RNAi mediated knock down of FGF-20 expression significantly suppressed the growth of mouse liver tumors. Downregulation of endogenous FGF-20 was confirmed by quantitative reverse-transcriptase PCR (Gibson et al., 1996, Genome Res. 6(10):995-1001). Tumors expressing FGF-20 shRNAs showed a reduced growth rate compared to parallel tumors expressing the control vectors. Tumor growth was assessed with calipers. These results indicate that FGF-20 is required for the efficient growth of liver tumors and thus may be therapeutic targets in a subset of human cancers.

EXAMPLE 3

Genomic and Immunohistochemical Overexpression of FGF-20 in Human Lung and Breast Tumors The presence of the FGF-20 amplicon in human lung tumors (shown in FIG. 1) suggests a broader role outside of liver cancer for FGF-20. To further explore this, we queried a compiled database of cancer gene expression studies (www.oncomine.org) and found that there was a significant correlation of FGF-20 expression with a particular subtype of Acute Myeloid Leukemia (AML). Notably, The molecular subtype of AML that is characterized by 11q23 translocations showed significantly lower expression than other molecular subtypes (Valk et al., supra). These data suggest that FGF-20 may be a therapeutic target for distinct subsets of human lung cancer.

A significant correlation of FGF-20 overexpression was also found to occur with metastasis in breast cancer (van de Vijver et al., 2002, N Engl J Med 347:1999-2009). To then examine whether the amplicon described in Example 1 resembles human breast cancer, immunohistochemistry was performed on a panel of breast cancer sections to examine the expression levels of FGF-20. Commercially available antibodies for R&D systems were used to identify FGF-20 expression.

As shown in FIG. 4, results indicated that FGF-20 protein is overexpressed in a significant proportion of breast cancer tumors (approximately 20%). This is approximately the same frequency of overexpression that was observed in liver cancer. These results suggest that FGF-20 is activated only in specific types of cancer.

We wanted to then determine in what subtype of breast cancer FGF-20 was overexpressed. To do this, we determined whole genome expression profiles of 38 different breast cancer cell lines, and looked to see if FGF-20 fell into a cluster of genes that were associated with a particular subtype of breast cancer.

Total RNA was isolated from breast cancer cell lines with Trizol (Invitrogen, CA), according to the manufacturer's instructions. For preparing the hybridization probes for the microarray experiments, RNA probes were generated with the MessageAmp II kit from Ambion (Austin, Tex.) and hybridized to Nimblegen microarrays (Homo sapiens Whole-Genome Expression Microarray) (Madison Wis.) following procedures recommended by the manufacturers. The microarrays were scanned with a 5 micron scanner (Axon Instruments) and the resultant image processed into numerical values with NimbleScan software (Nimblegen, Madison, Wis.). The numerical values were imported into BRB-Array Tools (BRB ArrayTools developed by Dr. Richard Simon and Amy Peng Lam at the NIH), which was used to perform all subsequent analysis.

Genomic representations were then produced from DNA obtained from several breast cancer cell lines and from normal breast tissue, fluorescently labeled and hybridized to microarrays. The data derived after scanning was normalized as described (Sebat et al., supra) and the resulting gene expression patterns were analyzed.

Figure 5:
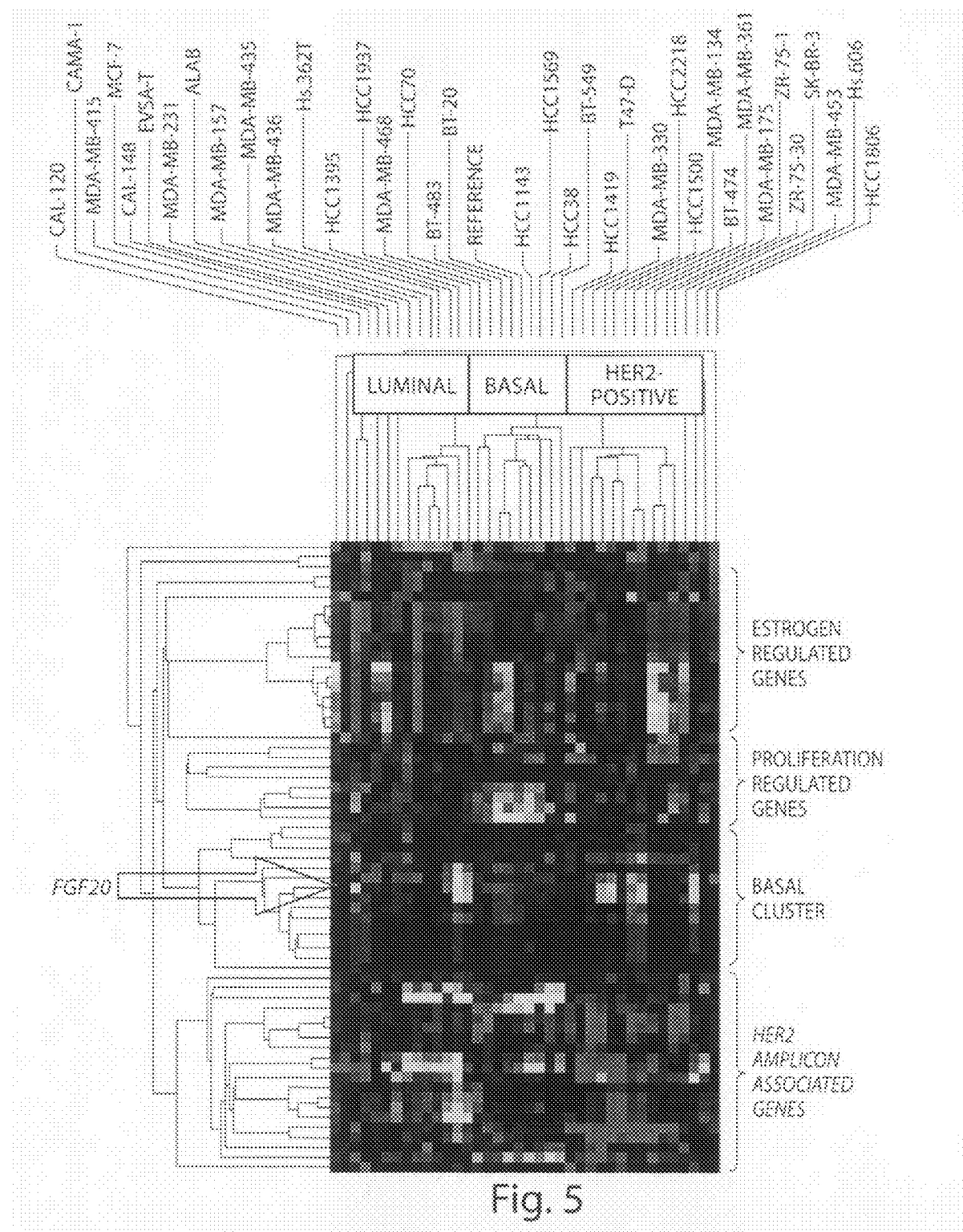
FIG. 5 is a diagram showing a whole genome expression profile. FGF-20 is overexpressed in the basal subtype of breast cancer, as determined by whole genome expression profiling and grouped by clusters comprising subtypes of cancer.
Figure 6:
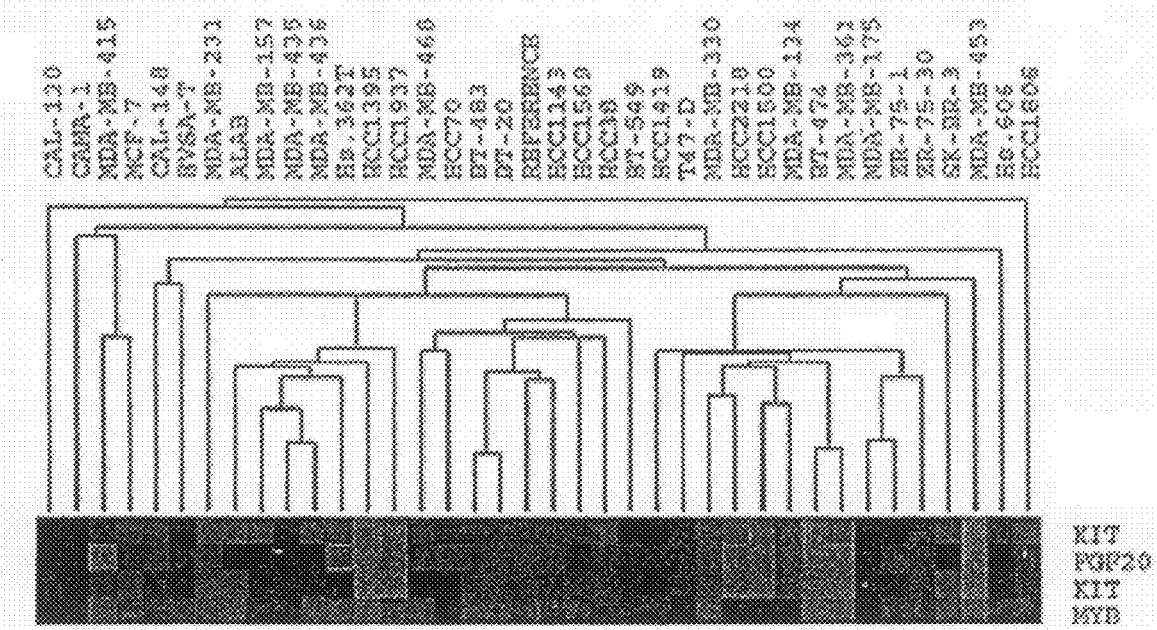
FIG. 6 is a diagram showing a partial genome expression profile. FGF-20 along with KIT is expressed in the basal cluster of genes in cell lines, along with MYB.

Gene classification of the genes differentially expressed between the three main subtypes of breast cancer (luminal, basal and HER2-positive) revealed different molecular mechanisms descriptive of the expression-based subtypes. As shown in FIG. 5 and FIG. 6, FGF-20 belongs to a cluster of genes (including KIT) that are associated with the basal subtype of breast cancer (Bryan et al., 2006, Mod Pathol 19:617-21; Nielsen et al., 2004, Clin Cancer Res 10:5367-74). This basal subtype is a highly lethal subtype that is in dire need of new therapeutics.

EXAMPLE 4

A Role for FGF-20 in Liver Regeneration

To test the hypothesis that FGF-20's oncogenic function could be a malignant manifestation of its normal role in stem cell self-renewal, we looked to see if FGF-20 is upregulated during liver generation.

FGF-20 mRNA levels were compared to untreated controls at 8, 24, 48, and 72 hours post hepatectomy. For each time point, two anesthetized mice received a centimeter long incision in the abdomen. The lower left and right lobes of the liver were pulled through the incision and ligated with surgical twine. Liver tissue below the twine was removed from the mouse. Partial removal of these two lobes yields approximately a 50% loss of total liver tissue. Removal of one upper lobe by the same method brings the total tissue loss to approximately 70%. Mice were sacrificed by asphyxiation in a CO2 chamber at time points post-surgery as indicated below. Remaining liver tissue above the ligation was harvested directly into Trizol and frozen at −80 until RNA extraction. Each time point harvests 1 control mouse and 2 mice that have undergone the ⅔ hepatectomy.

Figure 7:
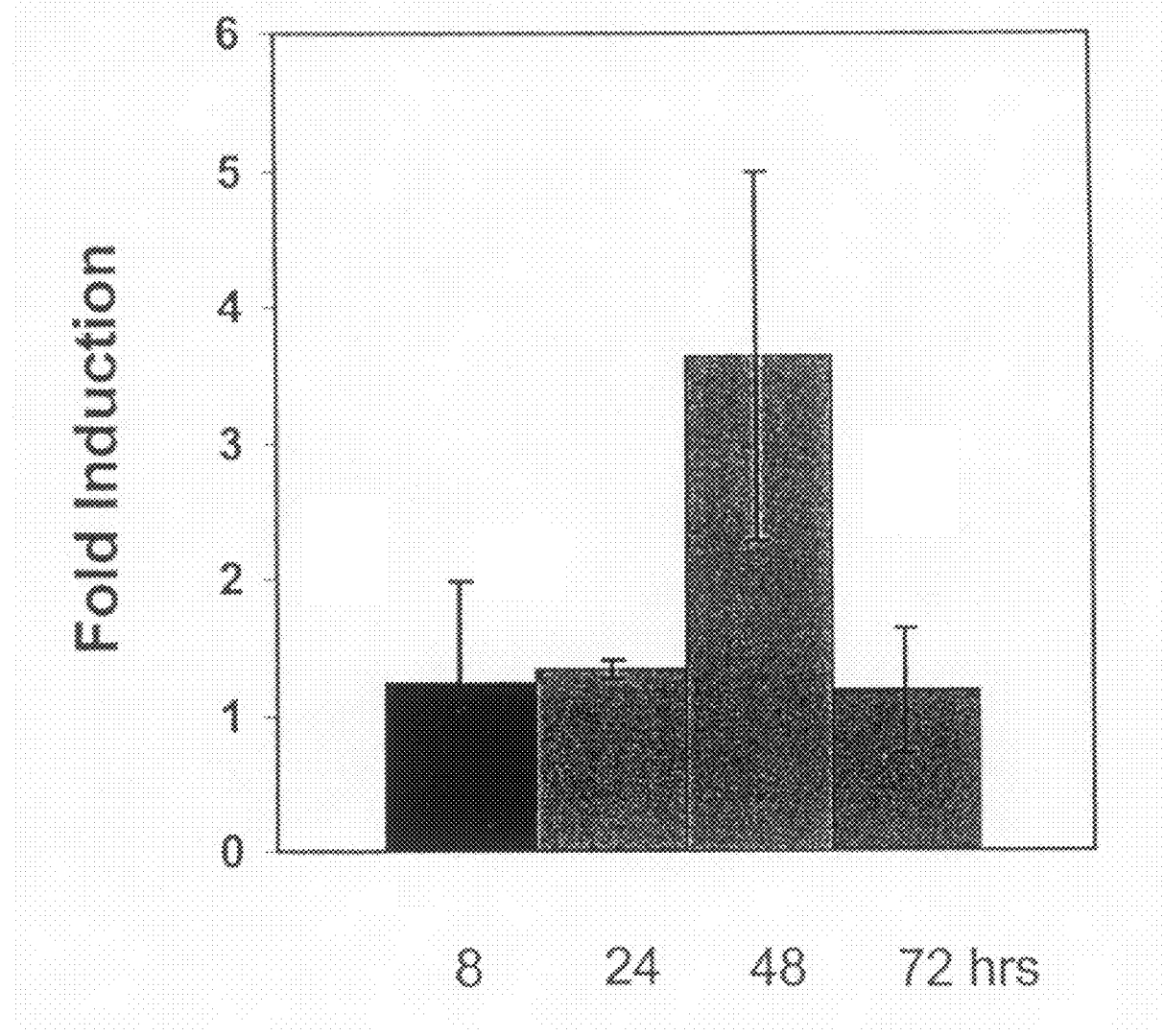
FIG. 7 is a bar graph showing FGF-20 levels over time in mice. FGF-20 mRNA levels were compared to untreated controls at 8, 24, 48, and 72 hours post hepatotectomy. For each time point, two anesthetized mice received a centimeter long incision in the abdomen. The lower left and right lobes of the liver were pulled through the incision and ligated with surgical twine. Liver tissue below the twine was removed from the mouse. Partial removal of these two lobes yields approximately a 50% loss of total liver tissue. Removal of one upper lobe by the same method brings the total tissue loss to approximately 70%. Mice were sacrificed by asphyxiation in a $CO_2$ chamber at time points post-surgery as indicated below. Remaining liver tissue above the ligation was harvested directly into Trizol and frozen at −80 until RNA extraction. Each time point harvests 1 control mouse and 2 mice that have undergone the ⅔ hepatectomy.

As shown in FIG. 7, FGF-20 was upregulated 48 hours following partial (70%) liver removal in the mouse. This was much beyond the wave of hepatocyte proliferation and coincided with the latter stages of liver regeneration, involving the reestablishment of normal liver tissue architecture (R. Taub. 2004. Liver regeneration: from myth to mechanism. Nat Rev Mol Cell Biol 5:836-47). These results demonstrate a role for FGF-20 in liver generation/regeneration and stem-cell self-renewal following injury. They also demonstrate a role for FGF-20 as a therapeutic target to enhance liver regeneration following surgical liver transplantation in humans in both the recipient and donor.

While this invention has been particularly shown and described with references to preferred embodiments thereof, it will be understood by those skilled in the art that various changes in form and details may be made therein without departing from the scope of the invention encompassed by these embodiments and the appended claims.

A description of certain preferred claims of the invention follows.

What is claimed is:

1. A method of diagnosing cancer in a human patient, comprising:
   (a) obtaining a DNA sample from the patient,
   (b) detecting amplification of an FGF-20 gene in the DNA sample, wherein amplification of the FGF-20 gene indicates the patient has cancer, and
   (c) after detecting amplification in step (b), diagnosing the patient as having cancer.

2. The method of claim 1, wherein the DNA sample is obtained from liver, lung or breast.

3. The method of claim 1, wherein the DNA sample is obtained from the colon.

4. The method of claim 1, wherein the cancer is Acute Myeloid Leukemia.

5. The method of claim 1, wherein detecting amplification of an FGF-20 gene comprises measuring the level of a nucleic acid that comprises the FGF-20 gene or a portion thereof in the DNA sample.

6. The method of claim 5, wherein measuring comprises performing a microarray analysis or a quantitative polymerase chain reaction to detect the nucleic acid.

7. The method of claim 5, wherein measuring comprises hybridizing a probe to the nucleic acid.

8. The method of claim 5, further comprising comparing the level of the nucleic acid to a control level of the nucleic acid.

9. The method of claim 8, wherein a level of the nucleic acid that is at least two-fold greater than the control level of the nucleic acid indicates that the nucleic acid is amplified in the DNA sample.

10. The method of claim 8, wherein the control level is the level of the nucleic acid in a DNA sample from a normal individual or healthy tissue.

11. The method of claim 5, wherein the nucleic acid is at least 20 nucleotides.

12. A method of detecting susceptibility to developing cancer in a human patient, the method comprising:
   (a) obtaining a DNA sample from the patient,
   (b) detecting amplification of an FGF-20 gene in the DNA sample, wherein amplification of the FGF-20 gene indicates that the patient is susceptible of developing cancer, and
   (c) after detecting amplification in step (b), detecting susceptibility to developing cancer in the patient.

* * * * *